United States Patent
Tissandier

(10) Patent No.: US 9,709,542 B2
(45) Date of Patent: Jul. 18, 2017

(54) BELL CAP AEROSOL ADAPTOR

(71) Applicant: HAMILTON SUNDSTRAND CORPORATION, Charlotte, NC (US)

(72) Inventor: Michael D. Tissandier, Alta Loma, CA (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 181 days.

(21) Appl. No.: 14/335,775

(22) Filed: Jul. 18, 2014

(65) Prior Publication Data

US 2016/0018374 A1    Jan. 21, 2016

(51) Int. Cl.
  *G01N 33/00* (2006.01)
  *G01N 1/22* (2006.01)
  *G01N 1/24* (2006.01)

(52) U.S. Cl.
  CPC ....... *G01N 33/0036* (2013.01); *G01N 1/2211* (2013.01); *G01N 1/2273* (2013.01); *G01N 1/24* (2013.01)

(58) Field of Classification Search
  CPC ...... G01N 33/0036; G01N 15/02; G01N 1/24; G01N 1/2211; G01N 1/2273; G01N 2001/245; G01N 2001/248; G01N 2001/2223; B01D 45/12; B01D 45/16; B04C 3/00; B04C 3/06; B04C 2003/006
  See application file for complete search history.

(56) References Cited

U.S. PATENT DOCUMENTS

| | | | | |
|---|---|---|---|---|
| 4,519,822 A | * | 5/1985 | Hatano | B04C 5/081 55/459.1 |
| 5,502,984 A | * | 4/1996 | Boehde | B01D 45/12 210/512.1 |
| 2003/0033890 A1 | * | 2/2003 | Rodgers | G01N 1/2211 73/863.43 |

* cited by examiner

*Primary Examiner* — Blake A Tankersley
(74) *Attorney, Agent, or Firm* — Snell & Wilmer L.L.P.

(57) ABSTRACT

A method of testing an air sample and/or testing equipment may comprise introducing aerosolized sample particles into an air flow to create sample air upstream from an air quality sampling device. The method may include introducing the sample air to an offset sample inlet of a bell cap inlet adaptor coupled to a sample tube. The method may include merging at least a portion of the introduced sample air with axially flowing air with little to no turbulence based on the geometry of the bell cap inlet adaptor and/or a containment cavity. The method may include introducing at least a portion of the sample air into the sample tube. Next, a test of at least one of the quality of the sample air and/or the functionality of the bell cap inlet may be performed.

8 Claims, 4 Drawing Sheets

BELL CAP AEROSOL ADAPTOR

FIELD

The present disclosure relates to testing systems, and more particularly to air quality detector testing systems.

BACKGROUND

The environment needed to make an accurate measurement of air quality (e.g., using a biological weapons detector testing system) often relies upon very large facilities to approximate open air scenarios. These large open facilities may be wasteful for the sample. Other restrictions in the containment vessel volume and geometry may introduce unwanted air turbulence.

SUMMARY

According to various embodiments, a bell cap inlet adaptor is disclosed herein. The bell cap inlet adaptor may comprise a sample inlet in air flow communication with a containment cavity. The containment cavity may be in fluid communication with an inlet to a sample tube. Air drawn through the sample tube may impart a cyclonic flow of air within the containment cavity. The sample tube may be offset from the axis of the containment cavity.

According to various embodiments, a method of testing an air sample and/or testing equipment may comprise introducing aerosolized sample particles into an air flow to create sample air upstream from an air quality sampling device. The method may include introducing the sample air to an offset sample inlet of a bell cap inlet adaptor coupled to a bell cap inlet. The method may include merging at least a portion of the introduced sample air with axially flowing air with little to no turbulence based on the geometry of the bell cap inlet adaptor and the bell cap inlet. The method may include introducing at least a portion of the sample air into the bell cap inlet. Next, a test of at least one of the quality of the sample air and/or the functionality of the bell cap inlet may be performed.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the disclosure, it should be understood that other embodiments may be realized and that logical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step.

Figure 1:
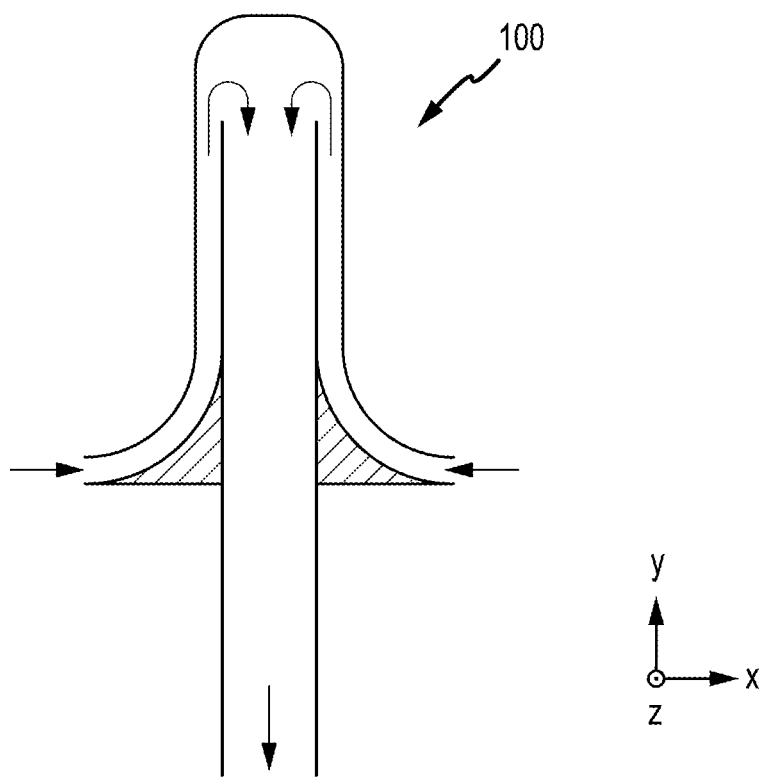
FIG. 1 depicts a cross-sectional illustration of a state of the art bell cap air quality and/or biological weapon detector testing system.

A common type of inlet for air quality and/or biological weapon detectors is the "bell cap" (See FIG. 1). Conventional bell cap inlet 100 testing systems have the advantage of being omnidirectional and easy to manufacture. Testing a system with a conventional bell cap inlet 100 in such a way as to control the sample losses is not trivial. Traditionally, a large enclosure that completely envelopes the conventional bell cap inlet 100 is used to ensure that aerosol losses due to turbulence are minimized. For systems with inlet flow rates in the hundreds of liters per minute, this enclosure (i.e., room built for testing the device) may be several feet across or losses of sample are observed. Indoor testing of these systems is often space constrained so a smaller interface that still allows losses to be minimized is utilized.

Thus, testing of air quality and/or biological detectors with a conventional bell cap inlet 100 is either very space intensive or subject to uncontrolled losses in sample efficiency. Use of the conventional bell cap inlet 100 also allows the losses inherent in the bell cap itself to be characterized independent of external effects such as wind speed or boundary layer conditions that may occur in an outdoor setting. It is desirable to develop a system and method to overcome these concerns.

Figure 2A:
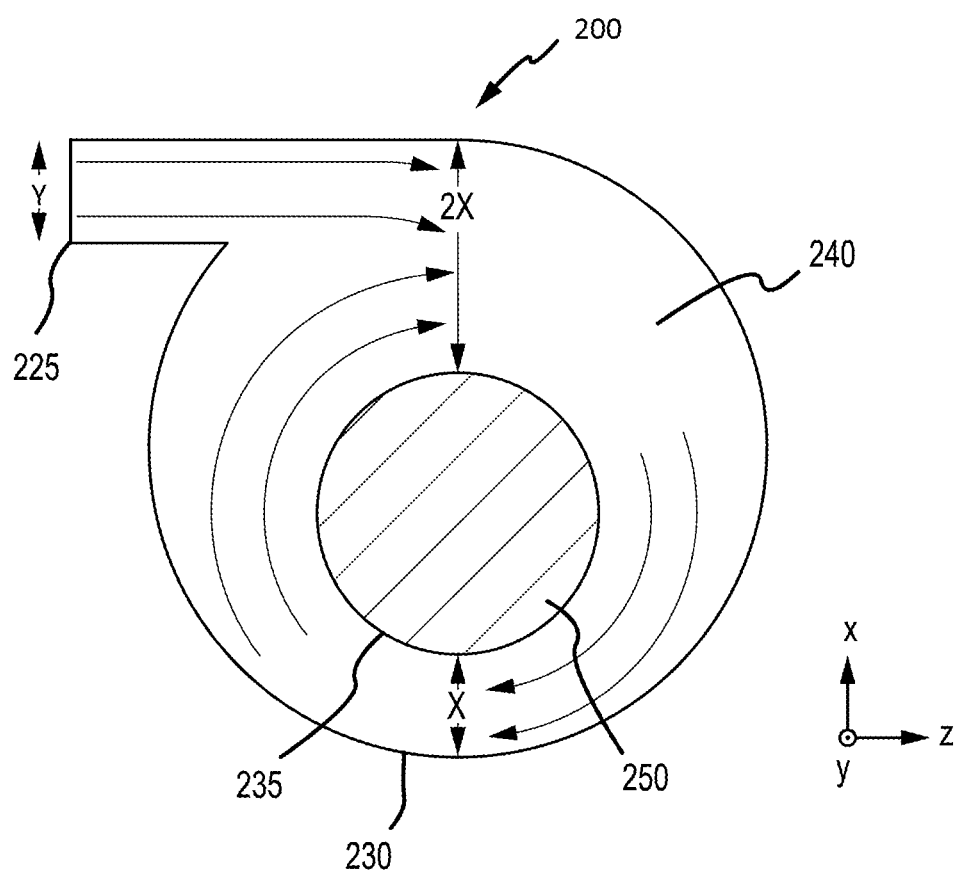
FIG. 2A depicts a cross-sectional top view illustration of a bell cap aerosol adaptor air quality and/or biological weapon detector testing system in accordance with various embodiments.
Figure 2B:
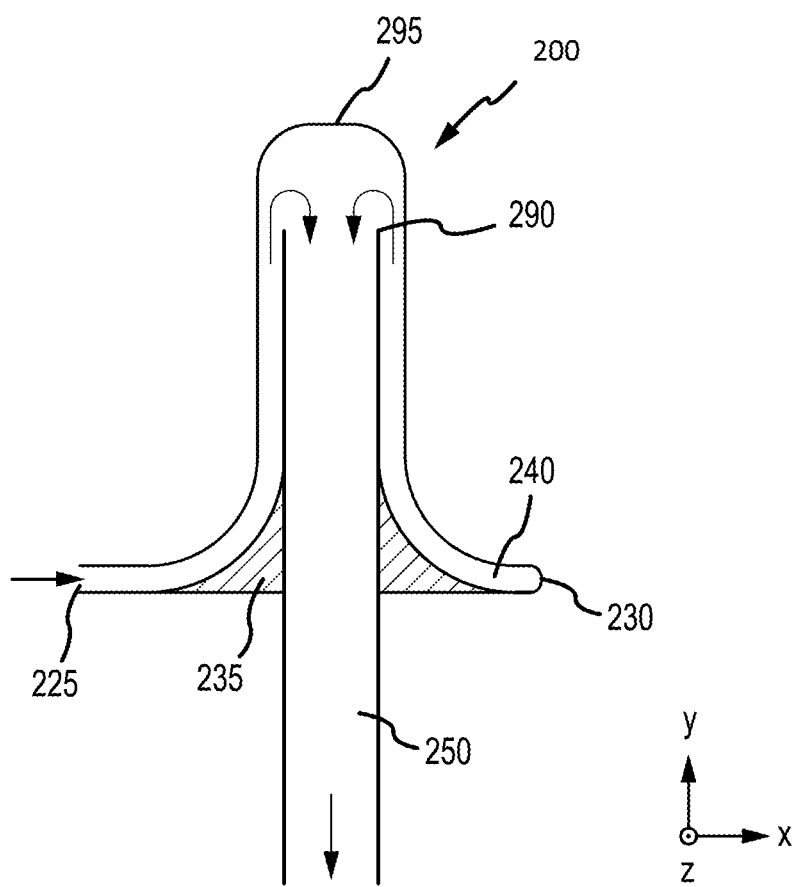
FIG. 2B depicts a cross-sectional side view illustration of a bell cap aerosol adaptor air quality and/or biological weapon detector testing system in accordance with various embodiments.

According to various embodiments and with reference to FIGS. 2A and 2B, a bell cap inlet adaptor 200 interface solves these and other concerns. Bell cap inlet adaptor 200 uses a velocity of incoming sample air and already present cyclonic flow within the bell cap inlet adaptor 200 to ensure aerosolized sample particles are driven to the sample tube inlet 290 of the sample tube 250 rather than lost to the peripheral structures of the bell cap inlet adaptor 200 or testing facility environment. In this way, the flows of air and the design of the shape of the containment cavity 240 minimize turbulence inside the containment cavity 240. The cyclonic flow of air within the containment cavity 240 may be due to an upstream fan or other device pulling air towards the rounded bell shaped top 295 of the bell cap inlet adaptor 200 to the sample tube inlet 290. The sample inlet 225 of the bell cap inlet adaptor 200 is tangentially offset to one side from the generally bowl shaped containment cavity 240 vessel. Stated another way, the sample inlet 225 may be contained within one quadrant formed by an X and Y plane passing through the center axis of the sample tube 250. In this way, the sample tube inlet does not surround the perimeter of the sample tube 250. The offset is such that sample air enters the sample inlet 225 and acts as a "sheath flow" against the air already present in the containment cavity 240. As used herein "sheath flow" refers to a flow of air with characteristics such that, when it merges with a second flow of air, it introduces minimal turbulence in the second flow of air. In this way, the flow of sample air entering sample inlet 225 flows seamlessly into the cyclonic flow of air within the containment cavity 240. Thus, the axial flow with the system, and in particular within the containment cavity 240, is substantially maintained in response to the sample air being introduced into the containment cavity 240 via the sample inlet 225. Sample inlet 225 may be a single location on a side of the bell cap inlet adaptor 200. This in contrast to the inlet location of a conventional bell cap inlet 100 which is in general, a circumferential slot which surrounds the internal sample tube 250. Stated another way, as can be seen in FIG. 2A, the sample inlet 225 may extend from the perimeter of the containment cavity 240 at a single location rather than around the around the perimeter of the sample tube 250 as in conventional bell cap inlets 100.

As mentioned above, the cyclonic flow rate of air within the containment cavity 240 may be a design constraint on the shape of the bell. The two flows (e.g., the flow entering sample inlet 225 and the concentric flow within containment cavity 240 around sample tube 250) are configured to be velocity matched to prevent and/or reduce the presence of turbulence and the accompanying loss of sample due to unintended interactions, such as unintended wall interactions within bell cap inlet adaptor 200 (surface 230 or outer surface 235 of sample tube 250). Sample tube 250 may be separate from and pass through (i.e. internal to) containment cavity 240. Vertically, the top of the containment cavity 240 is matched to the bottom of the bell cap inlet adaptor 200 to form a seamless interaction providing little to no dead space for sample loss.

The bell cap inlet adaptor 200 interface may be configured for particle size discrimination. In this way, bell cap inlet adaptor 200 interface is configured for testing at about the 1 to 10 micrometer (μm) level ($3.937 \times 10^{-5}$ inches to $3.937 \times 10^{-4}$ inches). Thus, the bell cap inlet adaptor 200 interface may be configured to substantially reject particles larger than about 10 microns (~0.00039 inches), as described in more detail below.

According to various embodiments and with continued reference to FIGS. 2A and 2B, a generally circular sample inlet 225 may be configured to receive sample air. This may be through a tube. Though they may be different distances, the width "Y" of the sample inlet 225 may be, in general, substantially equal to the distance from the outer surface 235 of sample tube 250 to surface 230 (See distance "X" of FIG. 2A).

The bell cap inlet adaptor 200 is configured for a continuous draw of air and/or sample air during a test. As the air and/or sample air enters sample inlet 225 a portion of the sample air makes a gradual turn up (in the Y direction as shown in FIG. 2B) into the neck of the bell cap towards the top 295 of the bell cap inlet adaptor 200, and a portion of the sample air follows the curve of the bell cap inlet adaptor 200 into containment cavity 240. Thus, as a portion of the combination of air and sample air is transferred up (in the Y direction as shown in FIG. 2B) and towards the top 295 of the bell cap inlet adaptor 200 a second, generally smaller portion of air and sample air follows the curve of the bell cap inlet adaptor 200 in the containment cavity 240. The design of the offset of the sample inlet 225 and the offset of the position of sample tube 250 within bell cap inlet adaptor 200 is configured to maintain axial flow and/or reduce turbulence of sample air entering the containment cavity 240. The distance from the outer surface 235 of sample tube 250 to surface 230 may be no larger than twice as large near the sample inlet 225 (See distance "2X" and distance "X" of FIG. 2A, where "X" depicts a minimum distance). The distance "X" may be be sized based on expected or intended flow rate.

In various embodiments, bell cap inlet adaptor 200 assists with the testing of the design of bell cap inlet 100. Bell cap inlet adaptor 200 may reduce the points of introduction of a sample to a single location (e.g., the sample inlet 225). In this way, the testing environment may be reduced significantly. Additionally, flow into the bell cap inlet adaptor 200 may be controlled.

Figure 3:
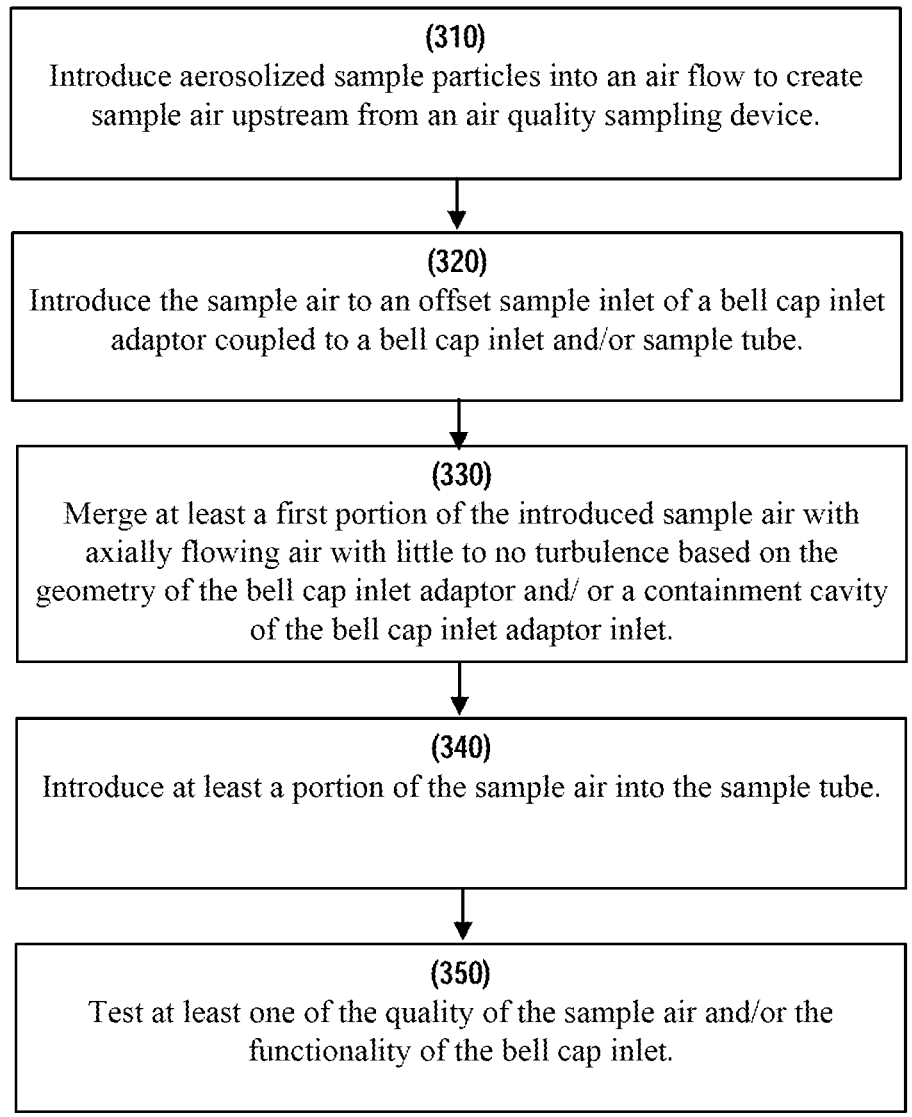
FIG. 3 is a flow diagram of a testing method via a bell cap aerosol adaptor air quality and/or biological weapon detector testing system in accordance with various embodiments.

According to various embodiments and with reference to FIG. 3, a method of testing an air sample and/or testing equipment may comprise introducing aerosolized sample particles into an air flow to create sample air upstream from an air quality sampling device (Step 310). The method may include introducing the sample air to an offset sample inlet of a bell cap inlet adaptor 200 coupled to a sample tube (Step 320). The method may include merging at least a portion of the introduced sample air with axially flowing air with little to no turbulence based on the geometry of the bell cap inlet adaptor 200 (Step 330). The method may include introducing at least a portion of the sample air into the sample tube (Step 340). Next, a test of at least one of the quality of the sample air and/or the functionality of the air quality sampling device, such as bell cap inlet adaptor 200, may be performed (Step 350).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments. Different cross-hatching is used throughout the figures to denote different parts but not necessarily to denote the same or different materials.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A bell cap inlet adaptor comprising:
    a sample inlet in fluid communication with a containment cavity;
    wherein the containment cavity is in fluid communication with an inlet to a sample tube,
    the sample inlet comprises a width being substantially equal to a shortest distance from an outer surface of the sample tube to an internal surface of the containment cavity,
    wherein air drawn through the sample tube imparts an axial cyclonic flow of air within the containment cavity,
    the sample tube is offset so as to not be concentric with the containment cavity, and
    a distance from the outer surface of the sample tube to an internal surface of the containment cavity at a location opposite the sample tube from a location of the shortest distance from the outer surface of the sample tube to the internal surface of the containment cavity, within a same horizontal plane, is no larger than twice the width of the sample inlet.

2. The bell cap inlet adaptor of claim 1, wherein the sample tube and the containment cavity have different center axes.

3. The bell cap inlet adaptor of claim 1, wherein the sample inlet is configured to merge the sample air entering the axial cyclonic flow of air within the containment cavity with minimal turbulence.

4. The bell cap inlet adaptor of claim 1, wherein the bell cap inlet adaptor interface is configured for about 1 to 10 micrometer particle size discrimination.

5. The bell cap inlet adaptor of claim 1, wherein the containment cavity is a bowl shaped containment cavity and the sample inlet is tangentially offset from the bowl shaped containment cavity.

6. The bell cap inlet adaptor of claim 1, wherein the distance from the outer surface of the sample tube to the internal surface of the containment cavity at the location opposite the sample tube from the location of the shortest distance from the outer surface of the sample tube to the internal surface of the containment cavity is no larger than twice as large as the shortest distance from the outer surface of the sample tube to the internal surface of the containment cavity, within the same horizontal plane.

7. The bell cap inlet adaptor of claim 1, wherein the sample inlet is contained within one quadrant formed by an X and Y plane passing through the center axis of the sample tube.

8. The bell cap inlet adaptor of claim 1, wherein a flow entering the sample inlet and the axial cyclonic flow of air within the containment cavity are configured to be velocity matched.

* * * * *